(12) United States Patent
Fodgaard et al.

(10) Patent No.: US 11,467,155 B2
(45) Date of Patent: Oct. 11, 2022

(54) SYSTEM AND METHOD FOR TIME-RESOLVED FLUOROIMMUNOASSAY DETECTION

(71) Applicant: Radiometer Medical ApS, Brønshøj (DK)

(72) Inventors: Henrik Fodgaard, Valby (DK); Olga Rodenko, Gentofte (DK)

(73) Assignee: Radiometer Medical ApS, Brønshøj (DK)

( * ) Notice: Subject to any disclaimer, the term of this patent is extended or adjusted under 35 U.S.C. 154(b) by 375 days.

(21) Appl. No.: 16/332,949

(22) PCT Filed: Sep. 6, 2017

(86) PCT No.: PCT/EP2017/072290
§ 371 (c)(1),
(2) Date: Mar. 13, 2019

(87) PCT Pub. No.: WO2018/050501
PCT Pub. Date: Mar. 22, 2018

(65) Prior Publication Data
US 2019/0360936 A1 Nov. 28, 2019

(30) Foreign Application Priority Data
Sep. 14, 2016 (DK) .............................. PA 2016 00533

(51) Int. Cl.
*G01N 33/543* (2006.01)
*G01N 33/68* (2006.01)
*G01N 33/53* (2006.01)
*G01N 21/64* (2006.01)

(52) U.S. Cl.
CPC ... *G01N 33/54366* (2013.01); *G01N 33/5302* (2013.01); *G01N 33/6887* (2013.01);
(Continued)

(58) Field of Classification Search
None
See application file for complete search history.

(56) References Cited

U.S. PATENT DOCUMENTS 6,469,311 B1 * 10/2002 Modlin .............. G01N 21/6408
250/559.4
6,483,582 B2 * 11/2002 Modlin .................. B82Y 15/00
250/458.1

(Continued)

FOREIGN PATENT DOCUMENTS

| CN | 101324574 A | 12/2008 |
|---|---|---|
| CN | 202126403 U | 1/2012 |

(Continued)

OTHER PUBLICATIONS

Babu, S. et al., "A PMMA microcapillary quantum dot linked immunosorbent assay (QLISA)," Biosensors and Bioelectronics, vol. 24, pp. 3467-3474 (2009).

(Continued)

*Primary Examiner* — Gailene Gabel
(74) *Attorney, Agent, or Firm* — Finnegan, Henderson, Farabow, Garrett & Dunner, LLP

(57) ABSTRACT

A system for time-resolved fluoroimmunoassay detection is disclosed. The system comprises a receptacle with a sample volume adapted for receiving a sample therein; a light source adapted to emit pulsed excitation light illumination optics adapted to collect the pulsed excitation light from the light source and to deliver the pulsed excitation light to the sample volume in the receptacle; a detection device adapted for gated detection of fluorescence radiation at least in a detection spectral range; detection optics adapted to collect fluorescence radiation from the receptacle at least in the detection spectral range and deliver the fluorescence radiation to the detection device; and an optical filter device (Continued)

configured for the separation of excitation light and detection light. A method for time-resolved fluoroimmunoassay detection is also provided.

8 Claims, 10 Drawing Sheets

(52) U.S. Cl.
CPC ..... *G01N 21/6408* (2013.01); *G01N 21/6428* (2013.01); *G01N 21/6452* (2013.01); *G01N 21/6456* (2013.01); *G01N 2021/6439* (2013.01); *G01N 2021/6471* (2013.01); *G01N 2201/062* (2013.01)

(56) References Cited

U.S. PATENT DOCUMENTS

| | | | | |
|---|---|---|---|---|
| 2008/0265177 | A1* | 10/2008 | Connally | G01N 21/6458 250/461.2 |
| 2015/0185150 | A1 | 7/2015 | Mathis et al. | |

FOREIGN PATENT DOCUMENTS

| | | |
|---|---|---|
| CN | 103105380 A | 5/2013 |
| CN | 103293133 A | 9/2013 |
| JP | 2008-517280 | 5/2008 |
| WO | WO 2006/089342 A1 | 8/2006 |

OTHER PUBLICATIONS

Bingqiang, Ren et al., "Design of time-resolved fluorometer based on immunochromatography," Proceedings of SPIE: International Conference of Optical Instrument and Technology, vol. 7157, pp. 71570Y-1-715707-7 (2009).

Bingqiang, Ren et al., "Time-resolved fluorometer based on immunochromatography," Chinese Journal of Scientific Instrument, vol. 30, No. 6, pp. 1330-1335 (2009).

Dayong, Jin et al., "How to Build a Time-Gated Luminescence Microscope," Current Protocols in Cytometry (2014) (36 pages).

Hagan, A.K. et al., "Lanthanide-based time-resolved luminescence immunoassays," Analytical and Bioanalytical Chemistry, vol. 400, pp. 2847-2864 (2011).

Zhang, Lixin et al., "Practical Implementation, Characterization and Applications of Multi-Colour Time-Gated Luminescence Microscope," Scientific Reports, vol. 4 (2014) (six pages).

Connally, Russell et al, "Solid-state time-gated luminescence microscope with ultraviolet light-emitting diode excitation and electron-multiplying charge-coupled device detection," Journal of Biomedical Optics, vol. 13, No. 3 (2008) (six pages).

Lu, Yiqing et al., "Time-Gated Orthogonal Scanning Automated Microscopy (OSAM) for High-speed Cell Detection and Analysis," Scientific Reports, vol. 2 (2012) (seven pages).

International Search Report for International Application No. PCT/EP2017/072290, dated Nov. 24, 2017 (four pages).

Written Opinion of the International Searching Authority of International Application No. PCT/EP2017/072290 (seven pages).

Hildebrandt, N., et al., "Luminescent terbium complexes: Superior Förster resonance energy transfer donors for flexible and sensitive multiplexed biosensing," *Coordination Chemistry Reviews*, 273-274, pp. 125-138, Jan. 28, 2014.

"Delfia & Lance," PerkinElmer Japan, Mar. 20, 2016 (two pages).

Rodekno, O. et al., "340 nm pulsed UV LED system for europium-based time-resolved fluoroescense detection of immunoassays," Optics Express, vol. 24, No. 19, pp. 22135-22143 (2016).

Valta, T. et al., "Ligand enabling visible wavelength excitation of europium (III) for fluoroimmunoassays in aqueous micellar solutions," Analytical Chemistry, vol. 84, No. 18, pp. 7708-7712 (2012).

\* cited by examiner a)

SYSTEM AND METHOD FOR TIME-RESOLVED FLUOROIMMUNOASSAY DETECTION

This application is a national stage filing under 35 U.S.C. § 371 of International Application No. PCT/EP2017/072290, filed on Sep. 6, 2017, which claims priority of Danish Patent Application No. PA 2016 00533, filed Sep. 14, 2016. The contents of these applications are each incorporated herein by reference.

TECHNICAL FIELD

The present invention relates in one aspect to a system adapted for time-resolved fluoroimmunoassay detection, the system comprising a receptacle with a sample volume adapted for receiving a sample therein; a light source adapted to emit pulsed excitation light; illumination optics adapted to collect the pulsed excitation light from the light source and to deliver said pulsed excitation light to the sample volume in the receptacle; a detection device adapted for gated detection of fluorescence radiation at least in a detection spectral range; detection optics adapted to collect fluorescence radiation from the receptacle at least in the detection spectral range and deliver said fluorescence radiation to the detection device; and an optical filter device configured for the separation of excitation light and detection light.

According to a further aspect, the invention relates to a method for time-resolved fluoroimmunoassay detection, the method comprising: immunostaining a sample with a lanthanide-chelate based fluorophore; illuminating the sample with an excitation pulse; waiting for a detection delay after termination of the excitation pulse; and detecting fluorescence radiation emitted from the sample in response to the pulse of excitation light during a detection period.

BACKGROUND OF THE INVENTION

Fluoro immunoassays are very useful and reliable tools in diagnostic analysis. Just for the sake of example, the detection and reliable measurement of the concentration of cardiac markers, such as Troponin, is extremely useful for identifying acute cardiac diseases. Therefore, it is desirable to make such measurements not only accessible to highly specialized sophisticated laboratory environments, but also provide such techniques at the point-of-care with a short turn-around time from sample taking to providing a useful measurement result. Such point-of-care apparatus typically requires easy operable, highly reliable devices providing unmistakable measurement results. Furthermore, whether located in a specialized laboratory or at the point-of-care, it is desirable that the apparatus for such assays is compatible with standardized or at least commonly used lab-ware for sample taking, handling and preparation. Compatibility with industry standards or at least with de-facto standards for sample taking, sample handling and sample preparation lab-ware, is also important within the apparatus itself, in order to be suited for integration of fluoroimmunoassay-based measurements within automated apparatus. This is even more the case, if the automated apparatus is adapted for measuring multiple parameters.

Fluoroimmunoassays are extremely challenging in terms of the sensitivity required to detect the presence of certain target substances, for example in a biological sample at relevant (very low) concentrations. Time-resolved fluorescence is a powerful tool that has been used in immunoassay detection to suppress short-lived background fluorescence and allow for high sensitivity. It relies on employing high-fluorescent fluorophores with long fluorescence lifetime and light sources emitting excitation pulses significantly shorter than the fluorescence lifetime of these fluorophores. Time-gated fluorescence detection delayed by microseconds with respect to the short excitation pulse exhibits improved signal-to-noise ratio (SNR) comparing to steady measurements as it reduces background of typical fluorescence lifetimes that are in range of nanoseconds. Many fluorophores with long fluorescence lifetime belong to the group of lanthanides. Europium is a lanthanide ion, which has been used as a marker in time-resolved fluorescence instruments due to its large Stokes shift and long fluorescence lifetime in the microsecond-(µs) to millisecond-(ms) regime. The excitation of lanthanide-based fluorophores for time-resolved detection techniques requires a pulsed UV light-source. For example, Europium is excited in the UV-A region and emits fluorescence with an emission peak at 616 nm.

However, as mentioned above, fluoroimmunoassays are extremely challenging in terms of the sensitivity required to detect the presence of certain target substances at relevant concentrations required in order to provide a useful diagnostic tool. Consequently, the detection of extremely low optical signals is required at levels competing with both noise and background radiation levels within the spectral range of the optical signal to be detected, and an efficient excitation of the target fluorophore is required. Therefore, Xenon flash lamps are commonly used as excitation sources for time-resolved fluoroimmunoassay detection, due to their powerful emission in short pulses in the nanosecond-regime, and further due to their spectral versatility resulting from a relatively broad band emission that can be tailored for specific fluorophores, e.g. using optical band pass filters. However, a main issue when using a flash lamp is its long trailing after-pulse afterglow for hundreds of microseconds that contributes to background emission and reduces SNR. As an alternative excitation light source, nitrogen lasers have been used but they are bulky, expensive, and operate at low repetition frequencies. More recently, UV LEDs have emerged as a light source for time-resolved excitation of fluorescent markers. However, such UV-LED's suffer from low power ratings and have, so far only been successful in applications where a comparatively high concentrations of fluorophore markers are present and where thus an abundant signal is available, for example, in the context of microscopic imaging or direct measurements of fluorescence lifetimes of fluorophores.

Therefore, there is a need for improved time-resolved fluoroimmunoassay detection that is compatible with implementation in an automated analysis apparatus.

Object of the present invention is therefore to provide an improved or at least alternative system and method for time-resolved fluoroimmunoassay detection overcoming at least some of the above-mentioned drawbacks.

SUMMARY OF THE INVENTION

A first aspect of the invention relates to a system adapted for time-resolved fluoroimmunoassay detection, the system comprising:
  a receptacle with a sample volume adapted for receiving a sample therein;
  a light source adapted to emit pulsed excitation light;
  illumination optics adapted to collect the pulsed excitation light from the light source and to deliver said pulsed excitation light to the sample volume in the receptacle;

a detection device adapted for gated detection of fluorescence radiation at least in a detection spectral range;

detection optics adapted to collect fluorescence radiation from the receptacle at least in the detection spectral range and deliver said fluorescence radiation to the detection device; and an optical filter device configured for the separation of excitation light and detection light; wherein the light source is a light emitting diode with a peak intensity emission at a wave length below 355 nm;

wherein the system further comprises a control unit configured to at least control timing of a detection cycle, the detection cycle comprising an excitation pulse emitted by the light emitting diode, followed by a detection period for the detection of fluorescence radiation by the detection device, wherein the detection period is separated from the excitation pulse by a detection delay; and wherein a pulse duration of the excitation pulse is at least 50 μs.

So far, to the best knowledge of the inventors, no successful implementation of time-resolved fluoroimmunoassay-detection using UV-LED's as a pulsed excitation source has been reported. This is, because light emitting diodes for the UV emission band have notoriously low peak power output as compared to e.g. flash lamps. Such a low power output requires very long pulses in order to achieve sufficient total pulse energy, i.e. a total pulse energy that is at least comparable to that provided by flash lamps. On the other hand, a very long excitation pulse strongly affects the excitation efficiency. A surprising insight of the present invention is that such a balance between the total excitation pulse energy and the efficiency of the excitation can actually be struck using an LED with a peak intensity emission wavelength below 355 nm, despite the very low peak powers emitted by such LEDs. In a further step, it has surprisingly been found that a pulse duration in the microsecond regime that is comparable to the fluorescence lifetime of the fluorophore can achieve reliable excitation in a time-resolved fluoroimmunoassay detection system, and even achieve improved signal-to-noise ratios as compared to a flash lamp based time-resolved fluoroimmunoassay detection system. Further surprisingly, it has been found that very good results are achieved for time-resolved fluoroimmunoassay detection when using lanthanide-based fluorophores, in particular europium-based (Eu-III) fluorophores, by using an LED with a peak intensity emission at a wavelength below 355 nm and with a pulse duration of at least 10 μs, preferably of at least 50 μs, and preferably below 500 μs. This is particularly surprising, since UV-LEDs in this wavelength regime, as mentioned previously, are notoriously known to have low power output. A lower limit of the pulse duration is governed by the consideration of achieving sufficient total pulse energy, whereas an upper limit for the pulse duration is governed by the consideration of achieving sufficient excitation efficiency. Further preferably, the pulse duration of the UV-LED with a peak intensity emission at wavelengths below 355 nm is selected between 100 μs and 400 μs, thereby further optimizing the balance between total pulse energy and excitation efficiency.

Most preferably, each of the LED excitation pulses have a minimum pulse energy delivered to the receptacle, wherein the minimum pulse energy is at least 2 μJ, at least 5 μJ, or even at least 10 μJ. Such a minimum pulse energy timely delivered to the sample is a requirement for achieving sufficient excitation in order to achieve useful signal to noise ratios for the very low signal levels of fluoroimmunoassay detection.

As recited above, a time-resolved fluoroimmunoassay detection system according to some embodiments comprises a receptacle, a light source, illumination optics, a detection device, detection optics, an optical filter device, and a control unit. The receptacle is for receiving an immunostained sample therein, wherein immunostaining is performed using a lanthanide-based chelate as a fluorophore. Preferably, the fluorophore is Europium-based. Under operation, the light source generates pulsed excitation light, which is collected by the illumination optics and delivered to a stained sample that has been prepared and placed in a sample volume in an inner volume or cavity, or at the bottom of the receptacle. In response to the pulsed excitation by the excitation light pulse, the fluorescent marker molecules in the immunostained sample emit fluorescent radiation with a characteristic spectral emission characteristic at wavelengths that are longer than the excitation wavelength (Stokes shift) allowing to spectrally distinguish between excitation light and fluorescence radiation. The excitation light and the fluorescent radiation are therefore separated from each other using an optical filter device, such as a dichroic filter set. The detection optics collects the fluorescence radiation emitted by the sample in the receptacle at least in a detection spectral range and delivers said fluorescence radiation to the detection device, which is adapted to detect fluorescence radiation at least within the detection spectral range.

After pulsed excitation, the emission of fluorescent radiation decays with a characteristic lifetime. The characteristic life time for much of the background radiation decays at a much faster rate than the radiation from lanthanide-based chelate fluorophores, in particular Europium-based chelate fluorophores. This allows separating the background fluorescence and the desired signal fluorescence radiation originating from the immunostained sample in time, by means of gated detection. Timing of the detection is therefore governed by the control unit according to a detection cycle. The control unit is configured to control timing of a detection cycle comprising an excitation phase, followed by a detection period separated from the excitation phase by a detection delay. The excitation phase starts when the excitation light source, here the LED, begins emitting excitation light (i.e. at the rising flank of the excitation pulse) and terminates after a pulse duration as controlled by the control unit. The detection delay starts at the termination of the excitation phase, and terminates at the beginning of the gated detection of fluorescence radiation. The beginning of the gated detection of fluorescence radiation marks the opening of a measurement window, which closes after the detection period has expired as determined by the termination of the gated detection. Measurements are thus acquired in a cyclic manner from a pulse train of excitation pulses, typically provided at a pre-determined repetition frequency. A post-detection delay may specify the time span between the termination of the detection period (i.e. closing of the measuring window) and the beginning of a new, subsequent excitation pulse. The length of a full detection cycle may thus be defined by the distance in time between corresponding points in subsequent detection cycles. For example, the time expiring from the rising edge of a first excitation pulse to the rising edge of a second, subsequent pulse. Typically, the excitation pulses are delivered in a periodic manner, i.e. at given frequencies determined by the sum of the pulse duration, detection delay, detection period and a post-detection delay.

Advantageously, a detection cycle is of the order of a few milliseconds, such as at least 1 ms, preferably at least 2 ms, or at least 3 ms, or at least 4 ms, or at least 6 ms, or even at least 8 ms. Accordingly the excitation pulses may be fired at a given frequency in the range between 10 Hz and 1 kHz, or in the range between 50 Hz and 500 Hz, or in the range between 100 Hz and 400 Hz. For a given detection delay and detection period a longer detection cycle means a longer post-detection delay. A longer post-detection delay has the advantage that long-lived background fluorescence is allowed to fully decay before the subsequent excitation pulse is fired, thereby further improving signal-to-noise ratio. To achieve proper timing, the control unit triggers/synchronizes the gated detection with respect to the excitation pulses according to the delays selected for the detection cycle.

It may be noted that an upper limit for the length of a detection cycle, and thus also for the length of the post-detection delay is the desire to accumulate within a given time as many reliable measurements as possible, i.e. the desire to perform as many viable detection cycles as possible within the given time. Such a given time can, for example, be determined by the total measuring time specified before a reliable result is to be provided by the system.

While the vast majority of measurements involving fluoroimmunoassay detection are performed at the limit of detectability as determined by the signal to noise ratio, the rare case of very high signal levels may occur due to a high concentration of biological markers, e.g. in samples from patients in a particular pathological state. Since the detection device is geared for very high sensitivity, in order to be able to collect extremely small fluorescence radiation signals close to the limit of detectability, such a high concentration of markers may lead to signal levels saturating the detection device or at least leading to a non-linear behavior of the detection output. The present system replacing a flash-lamp based excitation system with an LED-based excitation system has here a particular advantage, since it allows for adjusting the excitation pulse energy in an easy manner. As a consequence, in the rare case of a particularly elevated concentration of fluorescent markers in a sample, the pulse energy of the LED-excitation pulses may easily be reduced in order to keep the detection device in a linear regime. The system using an LED-based excitation thus achieves an improved dynamic range of the signal levels that can be handled by a given system as compared to flash lamp based systems.

Advantageously, the system may further comprise a data processor adapted for the collection and for the processing of output signals received from the detection unit representative of the fluorescence radiation detected by the detection unit.

Advantageously, according to some embodiments, the light emitting diode has a peak emission intensity of between 320 nm and 355 nm, further advantageously between 330 nm and 350 nm. Further advantageously, according to some embodiments, the light emitting diode has a spectral emission with a full width at half maximum (FWHM) between 10 nm and 20 nm. Thereby a good spectral overlap with lanthanide-based chelate fluorophores, and in particular with Europium-based chelate fluorophores, is achieved.

Further according to one embodiment of the system, the pulse duration of the excitation pulse is up to 500 µs. Advantageously according to some embodiments, the pulse duration of the excitation pulse is up to 400 µs. Further advantageously according to some embodiments, the pulse duration of the excitation pulse is at least 100 µs and up to 300 µs. By this choice of pulse durations, a surprisingly good signal-to-noise ratio is achieved striking a balance between the fluorescence lifetime of the above-mentioned lanthanide-chelate based fluorophores with an excitation pulse duration to optimize excitation efficiency. As mentioned above, most preferably, each of the LED excitation pulses have a minimum pulse energy delivered to the receptacle, wherein the minimum pulse energy is at least 3 µJ, at least 5 µJ, or even at least 10 µJ. Such a minimum pulse energy timely delivered to the sample is a requirement for achieving sufficient excitation in order to achieve useful signal to noise ratios for the very low signal levels of fluoroimmunoassay detection.

Further according to one embodiment of the system, the detection delay is between 200 µs and 600 µs, or preferably between 300 µs and 500 µs. By this choice of detection delays, a surprisingly good SNR is achieved, in particular in combination with the above and below specified particular ranges for the length of the detection period. The detection delay chosen from these ranges optimizes the SNR between short-lived background fluorescence, signal level due considering the decay according to the lifetime of the immunostaining fluorophore and long term background fluorescence. The delay is thus chosen sufficiently long such that the short lived background decays, yet no longer than that the fluorophore lifetime permits in order to maintain an appropriate signal level.

Further according to one embodiment of the system, the detection period is between 100 µs and 500 µs. This choice for the length of the detection period allows to accumulate signal, but not too long in order to avoid contribution from long lived background fluorescence affecting the SNR, due to signal decay of the lanthanide-based fluorophore as compared to the long lived background fluorescence.

Further according to one embodiment of the system the receptacle is a well. The well is similar to the type of wells known from microplates.

Advantageously, the receptacle is a well in a so-called microplate. Further advantageously, the microplate meets the Standards ANSI/SLAS 1-2004 through ANSI/SLAS 4-2004, as follows: ANSI/SLAS 1-2004: Microplates—Footprint Dimensions; ANSI/SLAS 2-2004: Microplates—Height Dimensions; ANSI/SLAS 3-2004: Microplates—Bottom Outside Flange Dimensions; and/or ANSI/SLAS 4-2004: Microplates—Well Positions. Further advantageously, the microplate meets the Standard ANSI/SLAS 6-2012: Microplates—Well Bottom Elevation The term 'microplate' as used herein refers to a flat plate with multiple "wells" used as small test tubes. The advantage of using microplate wells as receptacles for the fluoroimmunoassay detection is that microplates (also known as 'microtiter plate', 'microwell plate', or 'multiwell plate') are a widely used tool in analytical research and clinical diagnostic testing, e.g. for sample taking, handling and preparation. A fluoroimmunoassay detection system configured for using microplate wells as receptacles, is therefore compatible with common automation designs for laboratory equipment, thus facilitating integration/implementation in an automated analysis apparatus.

However, such an adaption of the fluoroimmunoassay detection to microplate wells entrains further challenges to the optical configuration, e.g. due to the fact that the optical access is restricted by the geometry of the wells themselves, which may be governed by standards or similar compatibility constraints. Further challenges may arise, e.g. due to the spatial requirements of other components of the apparatus accessing the receptacle Further according to one embodiment of the system, the illumination optics is an imaging optics projecting an image of the light emitting diode on an image plane in the sample volume. The illumination optics is thus arranged to project an image of the illumination source to an image plane overlapping the sample. Thereby it is achieved to meet the above-mentioned challenges to the optical configuration and facilitate integration and/or compatibility of the fluoroimmunoassay detection system with existing analysis apparatus, in particular automated analysis apparatus.

Further according to one embodiment of the system, the image plane coincides with a bottom plane in the receptacle/well. This configuration is particularly useful in the context of dried fluoroimmunostained samples located at the bottom of the receptacle/well. Dried fluoroimmunostained samples are e.g. prepared in order to avoid nonfluorescent decay pathways for the fluorophore that may occur in liquid samples, thereby increasing the quantum efficiency of the fluorophore.

Advantageously according to one embodiment of the system, the excitation imaging optics has an image-side focal length of more than 50 mm, and an image-side numerical aperture of below 0.4, alternatively an image-side focal length of more than 60 mm, and an image-side numerical aperture of below 0.3. Thereby an optical design is achieved allowing for the distant excitation of a sample in the sample volume under the mechanical constraints of a minimum distance between the excitation optics and a given sample plane.

Further advantageously, the illumination optics is optimized by balancing magnification against collection efficiency under the mechanical constraints of a pre-determined image-side numerical aperture in order to maximize the total energy delivered from the light emitting diode to the receptacle, and thus to the sample. Based on these considerations and the assumption that the light emitting diode can be described as a planar Lambertian emitter commercial ray-tracing software may be used in order to perform the optimization.

A second aspect of the invention relates to a method for time-resolved fluoroimmunoassay detection, the method comprising:
immunostaining a sample with a lanthanide-chelate based fluorophore;
illuminating the sample with an excitation pulse;
waiting for a detection delay after termination of the excitation pulse;
detecting fluorescence radiation emitted from the sample in response to the pulse of excitation light during a detection period;
wherein the excitation pulse is provided from a light emitting diode with a peak intensity emission at a wave length below 355 nm, wherein the excitation pulse has a pulse duration of at least 50 µs.

Further according to one embodiment of the method the fluorophore is a Europium-based chelate. The lifetime of the Europium-based chelate fluorophores are particularly well adapted for time-resolved fluoroimmunoassay detection with the above specified particular ranges for the excitation pulse, detection delay, detection period, post-detection delay and/or detection cycle. Furthermore the Europium-based chelate fluorophores provide a satisfactory fluorescence response for excitation in the UV-A band, and in particular in the range of the UV-A band from 320 nm up to 355 nm.

Further according to one embodiment of the method illuminating the sample includes providing the immunostained sample in a dried state in a sample plane and, by means of an illumination optics, generating an image of the light emitting diode in the sample plane.

Advantageously according to some embodiments, the excitation pulse has a duration of at least 100 µs, and/or up to 400 µs, or even up to 500 µs;

Advantageously according to some embodiments, the light emitting diode has a peak intensity emission at a wave length below 350 nm, preferably below 345 nm.

Advantageously according to some embodiments the light emitting diode has a peak intensity emission at a wave length of at least 320 nm, or at least 330 nm;

Advantageously according to one embodiment detecting fluorescence radiation includes, by means of detection optics, collecting fluorescence radiation emitted from the sample in response to the pulse of excitation light and delivering the collected fluorescence radiation to a detection device;

By the above described embodiments of a method for time-resolved fluoroimmunoassay detection, the same or analogue advantages are achieved as by the embodiments discussed above with respect to the system for time-resolved fluoroimmunoassay detection.

BRIEF DESCRIPTION OF THE DRAWINGS

Preferred embodiments of the invention will be described in more detail in connection with the appended drawings, which show schematically in FIG. 1 System for time-resolved fluoroimmunoassay detection according to one embodiment of the invention.

DETAILED DESCRIPTION OF PREFERRED EMBODIMENTS

In the following, one embodiment of a system 100 for time-resolved fluoroimmunoassay detection using a light emitting diode with a peak emission at 340 nm is discussed in detail. The system 100 is suited for use with standardized microplate receptacles 110 in an automated instrument with mechanical constraints for the minimum distance between the optics and the receptacle 110. In the following, the term 'receptacle' 110 and 'test cup', or just 'cup', are used interchangeably. Furthermore, data of a comparative study is presented comparing a system based on excitation with a 340 nm light emitting diode according to one embodiment of the invention, to a system using a Xenon flash lamp. The Xenon flash lamp is of a type commonly used in the prior art. The excitation optical system is designed to collect up to 80% of light emitted by an LED chip with a square shaped 1×1 $mm^2$ emitting surface with Lambertian emission characteristics. An LED image formed in the receptacle (cup) is 5×5 $mm^2$ in size which is three times larger than the image of the Xenon flash lamp used for comparison. The LED is operated at 370 mA with 200 μs pulse width and, at these operating parameters, delivers the same energy as the Xenon flash lamp. Temporal, spectral and spatial properties of the LED excitation of Europium-based chelates are investigated and discussed in the following.

Figure 1:
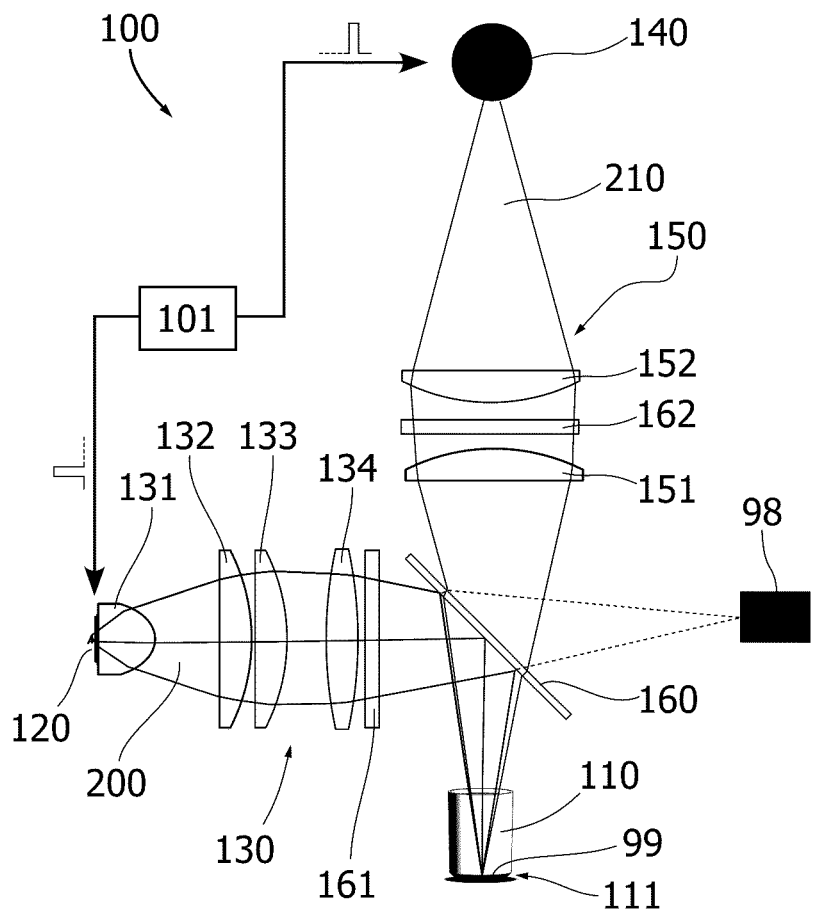
Figure 2:
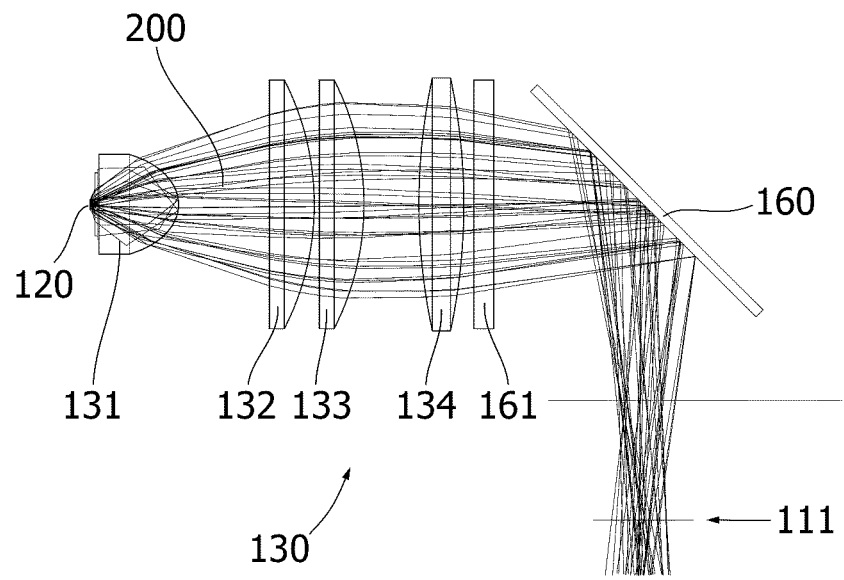
FIG. 2 Illumination optics according to the embodiment of FIG. 1.

Referring to FIG. 1 and FIG. 2, the optical system of the system 100 for time-resolved fluoroimmunoassay detection is now described. The optical system is a reflection-type fluorescence system and includes two subsystems with an excitation light path provided by illumination optics 130 and a detection light path provided by a detection optics 150, wherein a dichroic beam splitter 160 separates excitation and detection light paths.

In the first subsystem, the illumination optics 130, light is collected from a light emitting diode 120 (LED), which is considered as a Lambertian emitter with 1×1 $mm^2$ area by an aspheric lens 131 with focal length 8 mm and numerical aperture (NA) of 0.63. The next two plano-convex lenses 132, 133 of focal length 60 mm and biconvex lens 134 with focal length 67 mm form an image 65 mm away. All lenses 131, 132, 133, 134 of the illumination optics 130 are made of UV grade fused silica to ensure high transmission in UV-A region and minimize auto-fluorescence of lens material. The magnification of the illumination optics subsystem 130 is 5 and is limited by object and image side numerical apertures. The image is formed in the bottom of a test cup 110, which is made of polystyrene and is UV absorbing. The cup bottom is 6.7 mm in diameter and peripheral walls of the cup 110 are 10.6 mm in height, thus limiting image side numerical aperture (NA) for the center point to a value of 0.3, or 17.5 degrees. The illumination optics subsystem 130 is designed for maximum collection efficiency reaching 80%. In order to reduce system magnification, the first lens 131 would need to have to have larger focal length and thus smaller object side NA, or the last lens 134 would need to have shorter focal length, thus larger image side NA. The first option reduces the collection efficiency. Small acceptance angle of the test cup and a mechanical requirement of a minimum distance between beam splitter 160 and the test cup 110 make the second option not feasible. Thus, there is a trade-off between the magnification and collection efficiency. When excitation light 200 is delivered by the illumination optics 130 to a fluorescently stained sample 99 located in the receptacle 110, this causes the emission of fluorescence radiation 210 from the fluorophore in response to the excitation. The dichroic beam splitter 160 separates excitation 200 and detection 210 light paths. Emitted fluorescence light 210 is collected by two aspheric PMMA lenses 151, 152 in an arrangement of 1:1 magnification and is focused on a photocathode of a photomultiplier tube 140 (PMT). The PMT with a photocathode effective area of 8×24 $mm^2$ is used in photon counting mode. Two band-pass filters 161, 162 arranged in the excitation and detection subsystems 130, 150, respectively, ensure that only emitted fluorescence light 210 reaches the detector 140. A reference photodiode 98 is used to monitor the intensity of the excitation light 200.

Figure 3A:
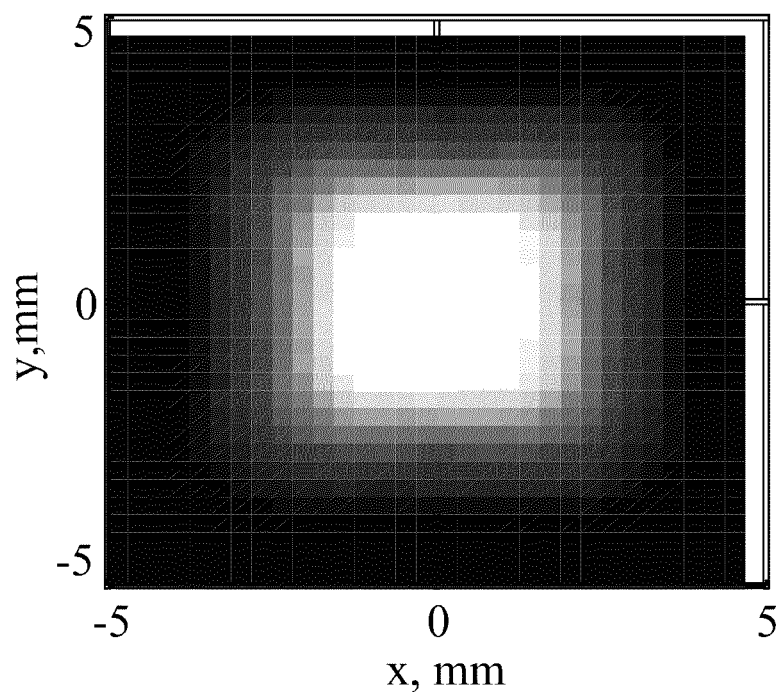
FIG. 3-5 (a) Images of excitation light sources formed in an image plane of the illumination optics and (b) corresponding cross-sectional normalized intensity distributions along x- and y-directions: simulated LED (FIG. 3), experimental LED (FIG. 4), and experimental Xenon flash lamp arc (FIG. 5)
Figure 3B:
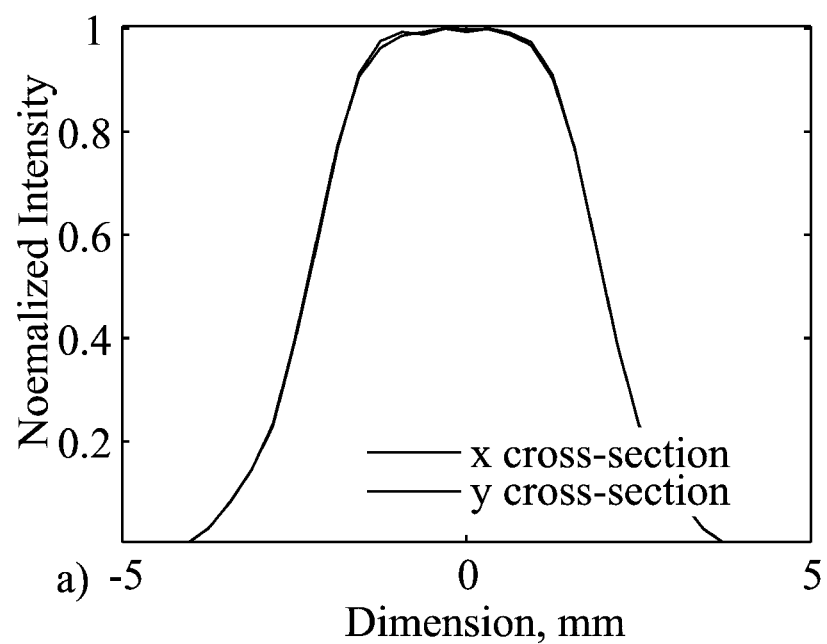
Figure 4A:
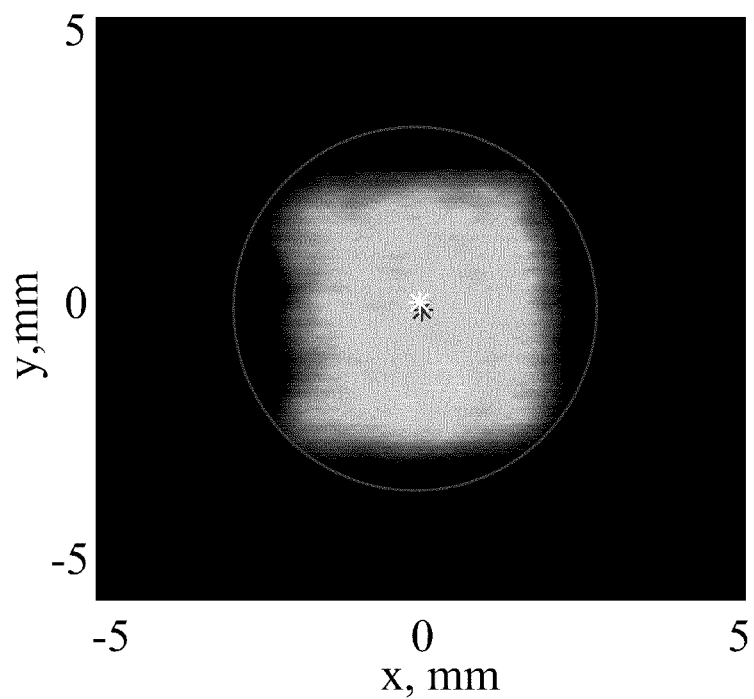
Figure 4B:
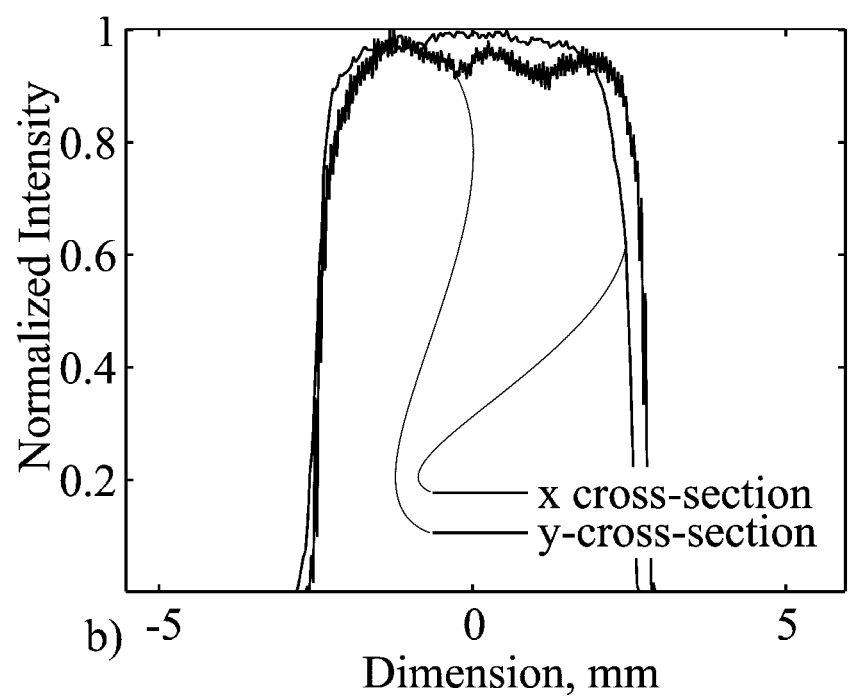
Figure 5A:
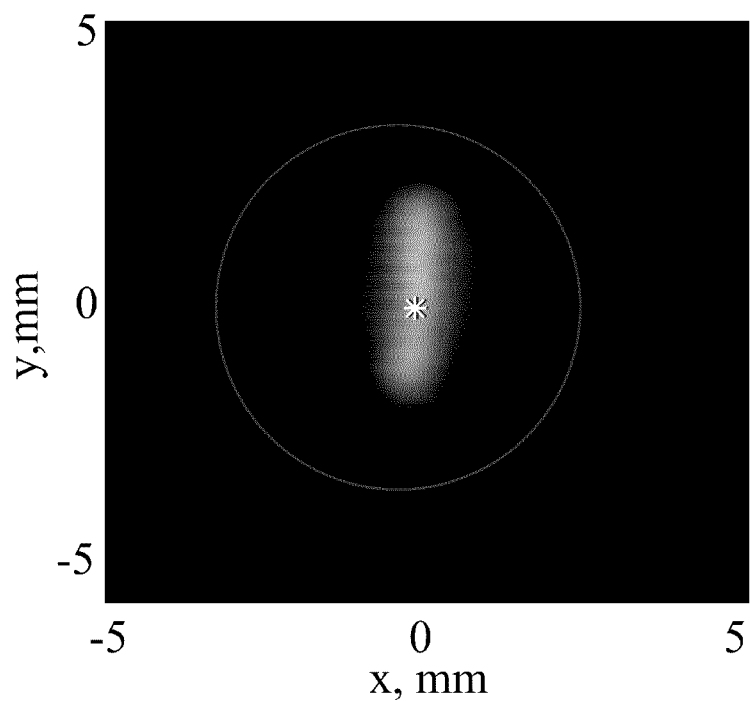
Figure 5B:
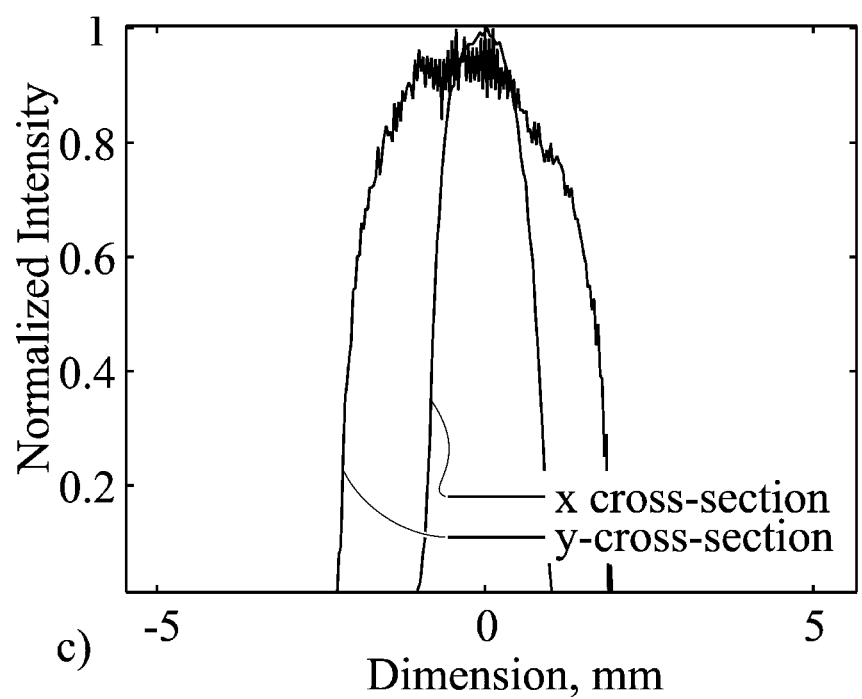

Referring to FIGS. 3-5, images of excitation light sources formed in an image plane of the illumination optics are characterized. FIG. 3a shows a simulated image of a planar, square LED with dimensions 1×1 $mm^2$. The image of the light source (LED) was obtained using commercial ray-tracing software. The image is square shaped with 90% of power encircled within a 5×5 $mm^2$ area. FIG. 4a shows an experimental image of a planar, square LED with dimensions 1×1 $mm^2$. The experimental image is generated at the bottom of the receptacle and was obtained using a camera. The experimental image of the LED is square-shaped with dimensions 5×5 $mm^2$ where low-intensity decaying edges are not seen due to limited dynamic range of the camera. FIG. 5a shows an experimental image of a Xenon flash lamp arc at the bottom of a receptacle. The image was obtained using the same camera. FIGS. 3b, 4b, and 5b show corresponding cross-sectional normalized intensity distributions along x- and y-directions in the image plane taken from the images of FIGS. 3a, 4a, and 5a, respectively. The image of the flash lamp arc is 2×4 $mm^2$ and thus covers an illumination area that is ⅓ of the four-fold symmetric LED image that covers 71% of cup bottom area. The image plane of the illumination optics is arranged within in the sample volume of the receptacle. In the case of a planar sample, the image plane is preferably arranged to coincide with a sample plane in the receptacle where the planar sample is located, e.g. for dried samples at the bottom in the receptacle 110.

Turning now to FIGS. 6-11, the excitation of a lanthanide-based fluorophore in an immunostained sample is described in more detail. In time-resolved fluorescence spectroscopy-based detection systems, the sample is illuminated with excitation light in the form of an excitation pulse. The light of the excitation pulse is absorbed by fluorophore molecules in the sample thereby bringing a number of fluorophore molecules in the excited state from which they can relax by emitting fluorescence radiation with a lifetime determined by the characteristics of the fluorophore. The emitted fluorescence radiation is spectrally separated from the illuminating excitation light, collected and delivered to detector, where it is measured. Lanthanide-based chelates have typical lifetimes in the range of a few hundred microseconds (μs) up to a few milliseconds (ms).

Figure 6:
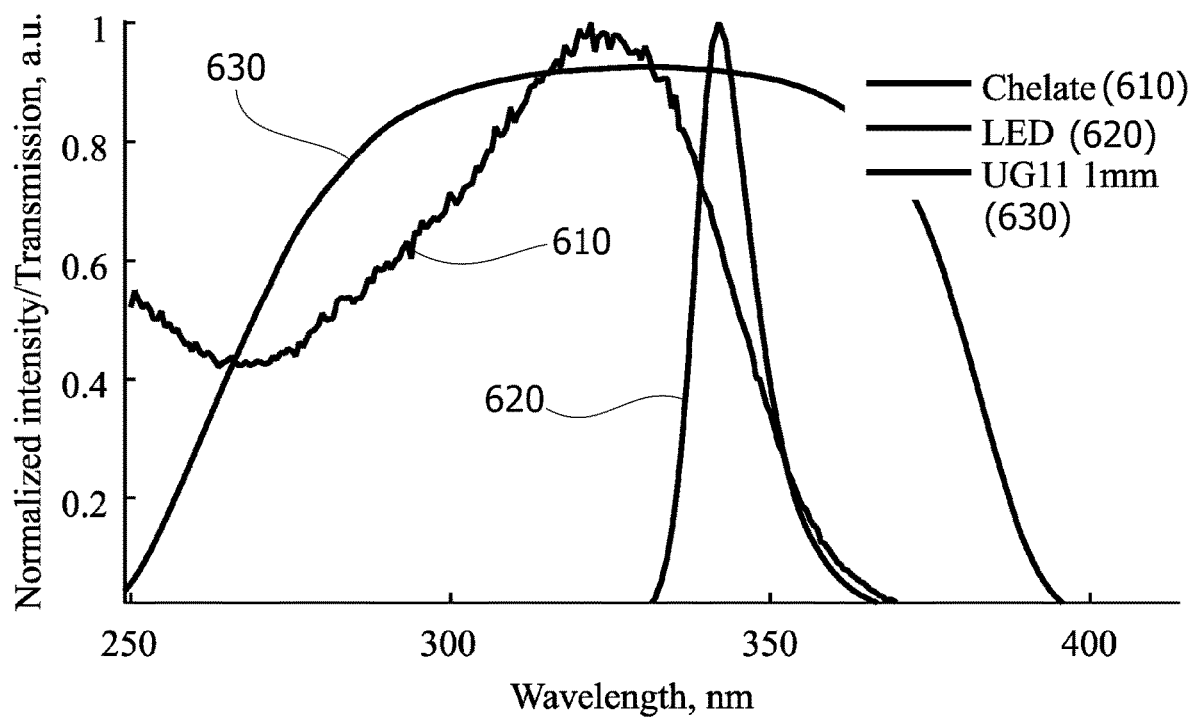
FIG. 6 a graph of the spectral characteristics of an Europium-based chelate fluorophore (Chelate), a light emitting diode (LED), and a band-pass filtered flash lamp (DUG11)

The spectral characteristics of the excitation system are shown in FIG. 6. The curve labelled 'Chelate' provides an example of an excitation spectrum 610 of a lanthanide-based chelate fluorophore. The particular fluorophore shown here is a Europium-based chelate 'a-Gal TEKES' from Radiometer Turku, Finland for Troponin-I cardiac markers, in the following also referred to as 'TnI-chelate'. The excitation spectrum 610 of the TnI-chelate has a peak at 325 nm with a full width at half maximum (FWHM) of 64 nm. The excitation spectrum 610 is normalized to its maximum value. It should be noted that different chelates can have slightly different excitation spectra with varying peak wavelength. Thus performance of the assays will vary when using a narrowband light source, such as an LED. The curve labelled 'LED' provides an example of the emission spectrum 620 of a light emitting diode. The emission spectrum 620 is also normalized to its maximum value. The LED emission spectrum 620 is centered at 343 nm with FWHM of 10 nm. When increasing LED current from 100 mA to 1 A in pulsed mode, no visual shift in peak wavelength was observed. Further analysis of the particular LED emission spectrum 620 employed here shows that normalized LED irradiance on a logarithmic scale drops to 1% and 0.1% of peak emission at 372 nm and 404 nm, respectively. The curve labelled 'UG11 1 mm' provides a transmission spectral characteristics of a band pass optical filter commonly used in combination with Xenon flash lamp based illumination systems, in particular a transmission spectrum of a DUG11 filter from Schott, 1 mm thick (Schott online library) (actually we use a 2 mm thick filter, but it's probably not relevant and too late to do anything about). A DUG11 filter from Schott filters out a 110 nm window of the flash lamp spectrum. The curve labelled 'UG11 1 mm' thus illustrates the emission spectrum 630 of a broadband Xenon flash lamp based illumination system. The LED emission spectrum 620 has 19% larger overlap with the chelate excitation spectrum 610 than the flash lamp illumination spectrum 630, assuming constant pulse energy.

Figure 7:
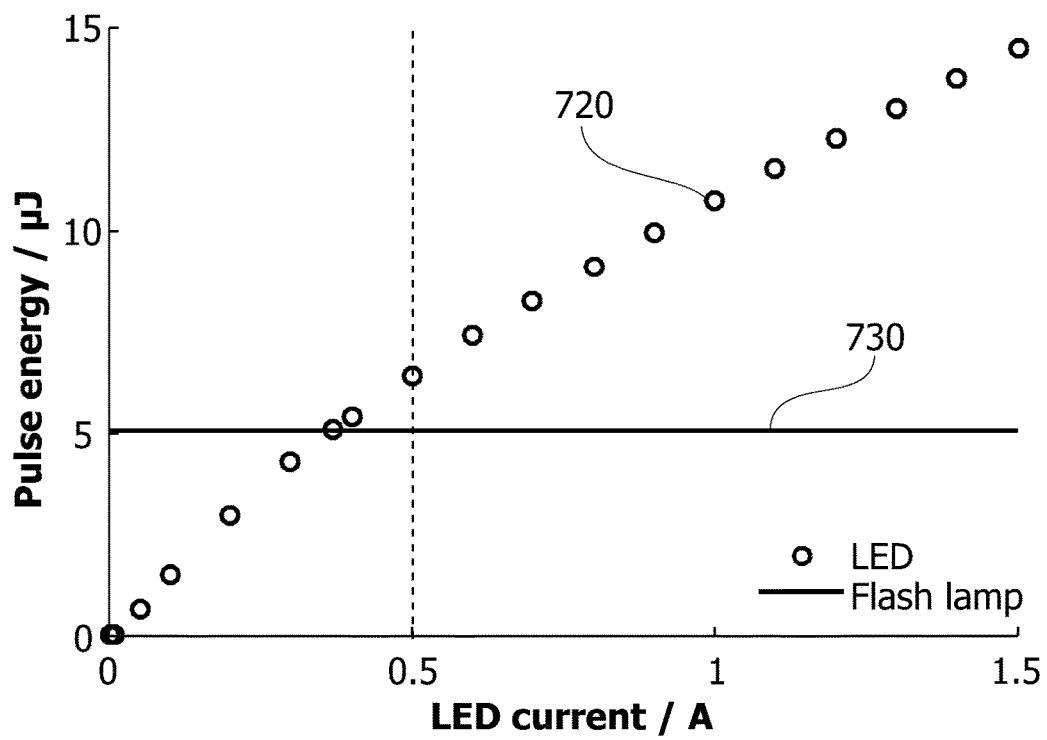
FIG. 7 a graph of the pulse energy emitted by the LED of FIG. 6 as a function of LED current.

FIG. 7 shows a graph illustrating the pulse energy that can be delivered to the receptacle. The data set labelled 720 (LED) shows the excitation pulse energy as a function of LED current, which can be delivered to the receptacle by the LED, when using an excitation pulse with a pulse duration of 200 μs and a duty cycle of 0.05. The Xenon flash lamp based illumination system delivers 5 μJ per pulse to the sample as indicated by the solid line 730. At a current of 370 mA, the excitation pulse energy delivered by the LED is equal to that of the Xe flash lamp based illumination system. By overdriving, the LED it is capable of delivering up to 15 μJ at a current of 1.5 A, which is three times the maximum injection current of 500 mA specified in the datasheet.

Figure 8:
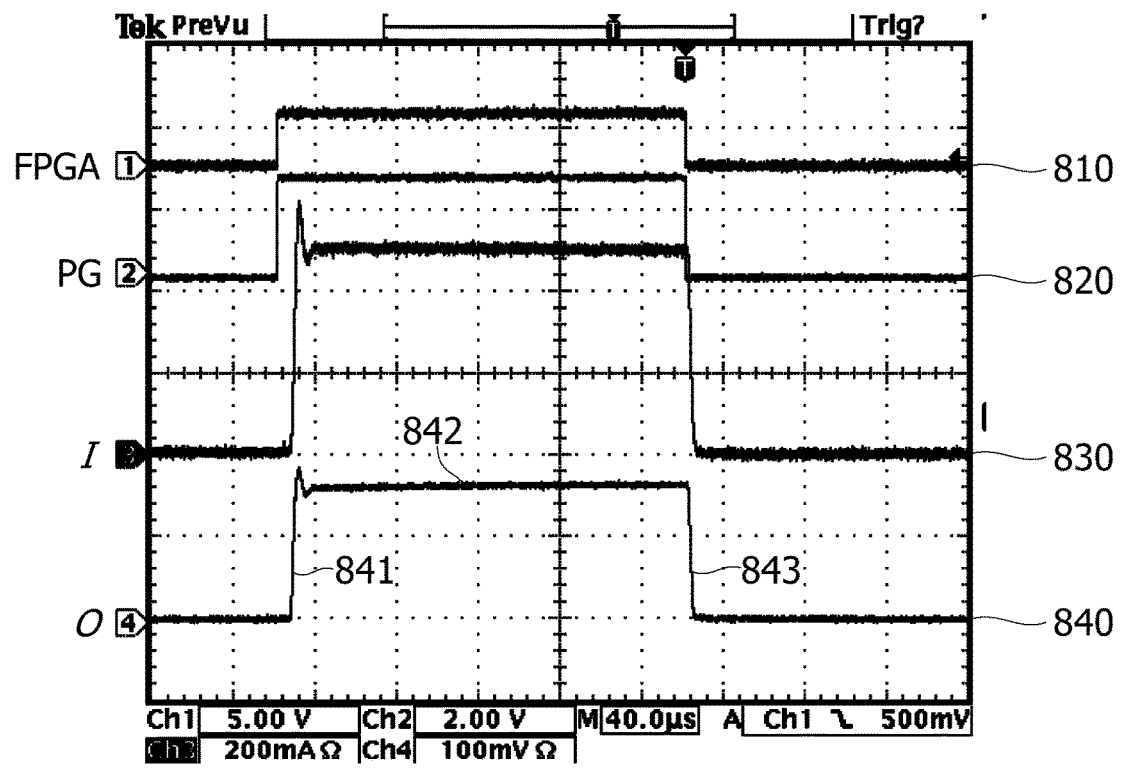
FIG. 8 a composite graph showing from top to bottom signals representative of: a trigger pulse from a field programmable gate array (FPGA), a trigger pulse from a pulse generator (PG) controlled by the FPGA, the resulting current in the LED circuit (I), and LED output power (O) as a function of time.
Figure 9:
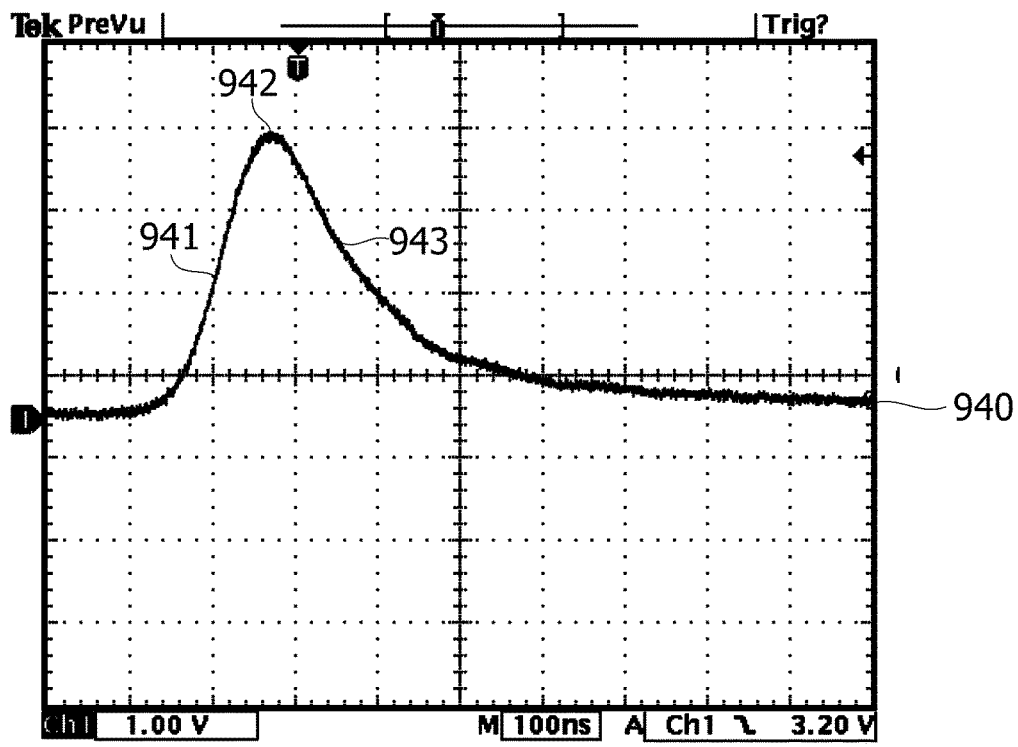
FIG. 9 a graph of the time-dependent power output of a Xenon flash lamp.

FIGS. 8 and 9 illustrate the temporal characteristics of the pulses as generated by the LED and Xenon flash lamp, respectively. FIG. 8 shows a composite graph with signals representative of (from top to bottom): a trigger pulse 810 from a field programmable gate array (FPGA), a trigger pulse 820 from a pulse generator (PG) controlled by the FPGA, the resulting LED current pulse 830 in the LED circuit (I), and an LED output power pulse 840 (O) as a function of time. The LED output power may, e.g. be monitored using a photodiode 98 in a set-up as shown in FIG. 1. The LED output power 840 is determined by the LED current 830. The LED output power pulse 840 is boxcar shaped with a rising edge 841, a plateau region 842 of essentially constant output power, and a falling edge 843. The duration between the first rising edge 841 and the final falling edge 843 is referred to as the pulse duration. The LED is controlled by an LED driver that is synchronized with the detection counting system. A commercially available driver from Thorlabs was used. The FPGA controls both excitation and detection systems with a trigger pulse train. It goes to the LED driver through the pulse generator (PG) and the LED is switched on. The LED pulse duration is 200 μs, which is three orders of magnitudes longer than the flash lamp pulse duration of 200 ns, see FIG. 9 and below. The LED pulse duration has to be smaller than the fluorophore lifetime, at the same time delivering enough excitation energy in order to bring a sufficient number of fluorophore molecules into the excited state to produce a detectable optical signal. With the driver circuit used here, the minimum pulse duration is about 5 μs. However, shorter pulse durations can be achieved with special driver circuits, if desired. A delay of 8 μs between the trigger pulse 810 and the LED current pulse 830 is observed. The fall time of the LED pulse is smaller than 3 μs. FIG. 9 shows a graph of the time-dependent power output of the Xenon flash lamp illumination system. The flash lamp has a pulse-duration of 200 ns and a fall time of 400 ns (90%-10%).

Figure 10:
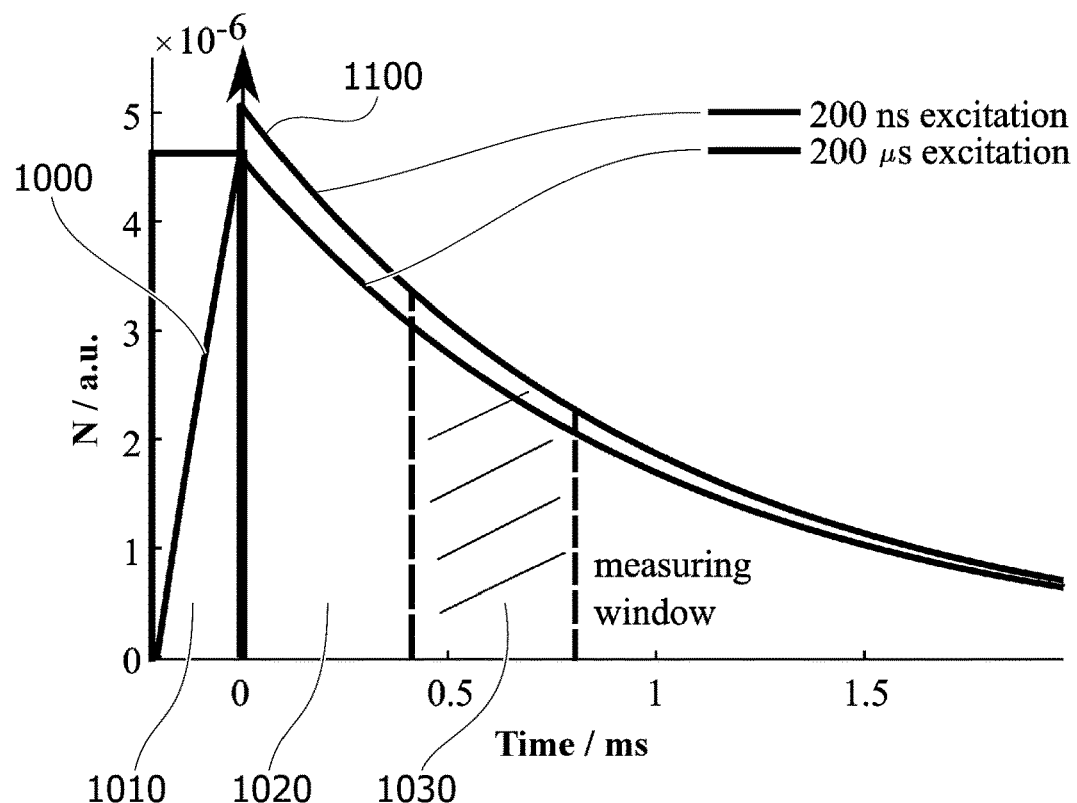
FIG. 10 a graph of a detection cycle with calculated curves for the number of excited fluorophore molecules for two different excitation pulses.
Figure 11:
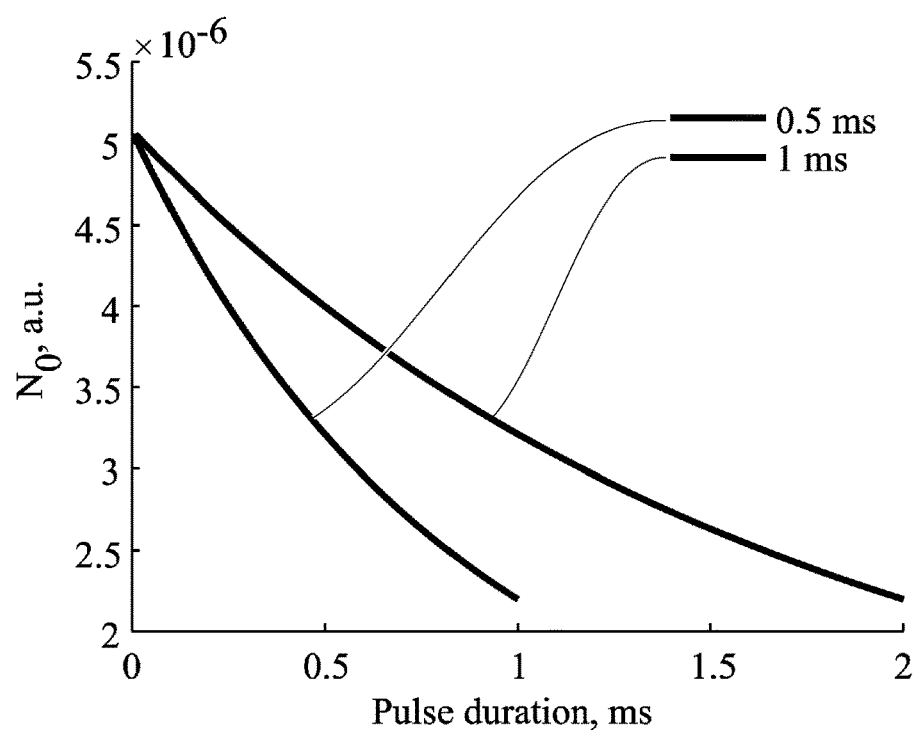
FIG. 11 a graph of the calculated number of excited fluorophore molecules immediately after termination of the excitation pulse for two different excitation pulses.

Referring to FIG. 10 and FIG. 11, the effect of pulse duration and fluorescence lifetime on the number of excited fluorophore molecules is discussed. As mentioned above, understanding the relevance of this relation is important in order to identify useful ranges for the timing of the excitation and detection cycles, in particular for determining a useful range for the pulse duration of the LED excitation pulses. As also mentioned above, the much longer LED pulse duration affects the excitation efficiency of chelates. The LED pulse duration is comparable to the fluorescence lifetime of lanthanide-based chelate fluorophores, in the range of hundreds of microseconds, whereas a flash lamp pulse is in the range of hundreds of nanoseconds. The number of excited molecules is smaller in the first case as further detailed in the following. The population of excited molecules N follows the rate equation:

$$\frac{dN}{dt} = \alpha \cdot P(t) - k \cdot N, \quad (1)$$

where P(t) is excitation pulse peak power; k is rate constant of fluorophore (inverse proportional to fluorescence lifetime τ). The number of molecules No when the excitation pulse is switched off is $$N_0 = \alpha \cdot \frac{P(t)}{k} \{1 - \exp(-k \cdot \tau_p)\}, \quad (2)$$

The decay of excited molecules follows:

$$N(t) = \alpha \cdot P(t) \cdot \tau \left\{1 - \exp\left(\frac{-\tau_p}{\tau}\right)\right\} \cdot \exp\left(\frac{-t}{\tau}\right), \quad (3)$$

With longer excitation pulse the number of excited molecules is smaller for equal pulse energy. FIG. 10 shows the time-dependent number of excited molecules N when illuminated by an excitation pulse of 200 ns and 200 μs (curves 1100 and 1000, respectively). N grows exponentially during the pulse with a coefficient proportional to the excitation peak power and starts decaying exponentially with the lifetime T, here 1 ms, when the pulse is switched off. This curve can also be obtained by convolution of excitation pulse and fluorescence decay. The difference in pulse duration of three orders of magnitude in this case corresponds to a 10% decrease of the number of excited molecules, and thus of the fluorescence signal. The correlation between pulse duration and the decreasing number No of excited molecules at the end of the excitation pulse is demonstrated in FIG. 11. Curves for two different fluorescence lifetime values of 0.5 ms and 1 ms, respectively, are shown. In FIG. 11, the pulse duration is varied under the constraint of keeping the total pulse energy constant. The longer the excitation pulse, the smaller the number of excited molecules at the end of the excitation pulse.

A measuring window 1030 is opened after a detection delay 1020, by sending a gate signal to detection device activating the counting system during a detection period. Typically, when using a flash lamp based illumination system, a detection delay of 400 µs is used in order to achieve a sufficient decay of short-lived background fluorescence. Comparative measurements using LED-excitation are therefore also performed with a detection delay of 400 µs. The detection delay 1020 of 400 µs is between the excitation pulse 1010 and the detection period marking the measurement window 1030. Surprisingly, the inventors have found that the detection delay may be reduced with respect to the 400 µs when using LED-based illumination, since background counts appear to decay more rapidly to an 'acceptable' level, when exciting with the LED. As a consequence of a shorter detection delay, the fluorescence signal from the lanthanide-based tracer fluorophore has decayed less when the measurement window is opened, and thus the signal-to-noise-ratio obtained with LED-excitation is further improved. For example, the detection delay may be reduced down to 300 µs.

Referring in particular to FIGS. 12-16 in the following, a detailed example is given for fluoroimmunoassay detection with samples of a cardiac marker Troponin-I (TnI) with 200 ng/L concentration including comparison between the LED-based excitation according to the above-mentioned embodiment of a system for fluoroimmunoassay detection on the one hand, and traditional Xenon flash lamp based excitation on the other hand. The background of the system includes PMT dark counts, auto-fluorescence from the optical unit itself, polystyrene and non-specific binding. The background, measured with blank cups processed with null concentration solution, is reduced when excited by LED, due to absence of flash lamp decaying edge, longer excitation pulse duration and shorter fluorescence lifetime of background, and worse spectral match of narrow band UV light (10 nm) with background excitation spectrum, in comparison to a more broadband flash lamp spectrum (100 nm). Hence, the signal-to-background ratio is improved by 18%. It may be noted that in this particular configuration, the fluorescence signal was decreased by 26% when excited by the LED based system for the same exposed energy (i.e. the same total pulse energy). The three orders of magnitude longer excitation pulse of the LED based system decreases signal by 10%. Non-uniform spatial distribution of fluorescence chelates in the receptacle further decreases the fluorescence response. Thus the SNR of the system was decreased by 15%. Generally, the SNR can be improved by increasing the excitation light energy. For constant excitation energy, SNR can be improved by reducing the illumination area, having a shorter excitation pulse width and, if possible, a better spectral match with the chelate excitation spectrum. The standard deviations of signal and blank cups are in the same range as for the flash lamp. As further detailed in the following example, the present invention provides a viable solution for using an LED based excitation instead of flash lamp excitation in time-resolved fluoroimmunoassay detection.

Example

In this example, the LED based system is used to test its capability in time-resolved fluorescence immunoassay measurements of a Troponin I (TnI) cardiac marker. Fifteen sample cups and fifteen blank cups were produced for the experiment with TnI immunoassay. The TnI cups are made of polystyrene coated by streptavidin to block non-specific bonding of tracer antibodies. A layer of capture antibodies in the bottom is used to capture the antigen in the sample between the tracer and capture antibodies. Europium fluorescent marker is bound to the tracer antibodies, which are placed in the cup closer to the sides. An insulation layer prevents contact between the capture and tracer antibodies. A sample cup is processed with a 10 µL reference solution with the TnI concentration of 200 ng/L. During the incubation, it is heated to 36° C. for 15 minutes and shaked to reduce the reaction time. After the reaction, the cup is washed and unbound tracer antibodies are washed out. The labeled tracer antibodies bound to the antigen are then excited by UV light source and emit light with a peak emission at 616 nm. A blank cup is processed in the same way but with a solution of null TnI concentration. The counts measured on the blank cups are called background counts. An optical unit based on the currently used Xenon flash lamp was used for comparison. The unit has different excitation optics but the detection light path is the same. The standalone flash lamp unit was adjusted and calibrated before the experiment to a known standard. LED current of the LED based optical unit was adjusted to deliver the same energy per pulse as the flash lamp unit. Each cup was measured consequently on flash and LED without rotation, in the same cup holder.

There are different definitions of SNR used in literature. We define SNR as signal corrected for averaged background value, divided by the sum of signal and background variations $$SNR = \frac{\bar{S}(200 \ ng/L) - \bar{B}(0 \ ng/L)}{\sqrt{\sigma_S(200 \ ng/L)^2 + \sigma_B(0 \ ng/L)^2}}, \quad (4)$$

where $\bar{S}$ is signal averaged over N sample cups, $\bar{B}$ is background averaged over N blank cups, $\sigma_S$ and $\sigma_B$ are standard deviations of the signal and background, respectively. Thus, both signal and background variation are taken into account. Dark counts of PMT are neglected in the equation. In turn, we define signal-to-background ratio as relation of averaged signal to average background $$S/B = \frac{\bar{S}(200 \ ng/L)}{\bar{B}(0 \ ng/L)}, \quad (5)$$

The background of the system includes PMT dark counts (less than 10/25° C.), background from the optical unit itself (auto-fluorescence from materials and contamination) and from the cup (polystyrene, streptavidin coating, non-specific binding, contamination). Moreover, we distinguish background from an empty cup (polystyrene only) and blank cup (processed with null concentration solution). The latter contains chemical layer with antibodies in the bottom, as discussed above, and all tracer antibodies are washed away ideally.

Figure 12:
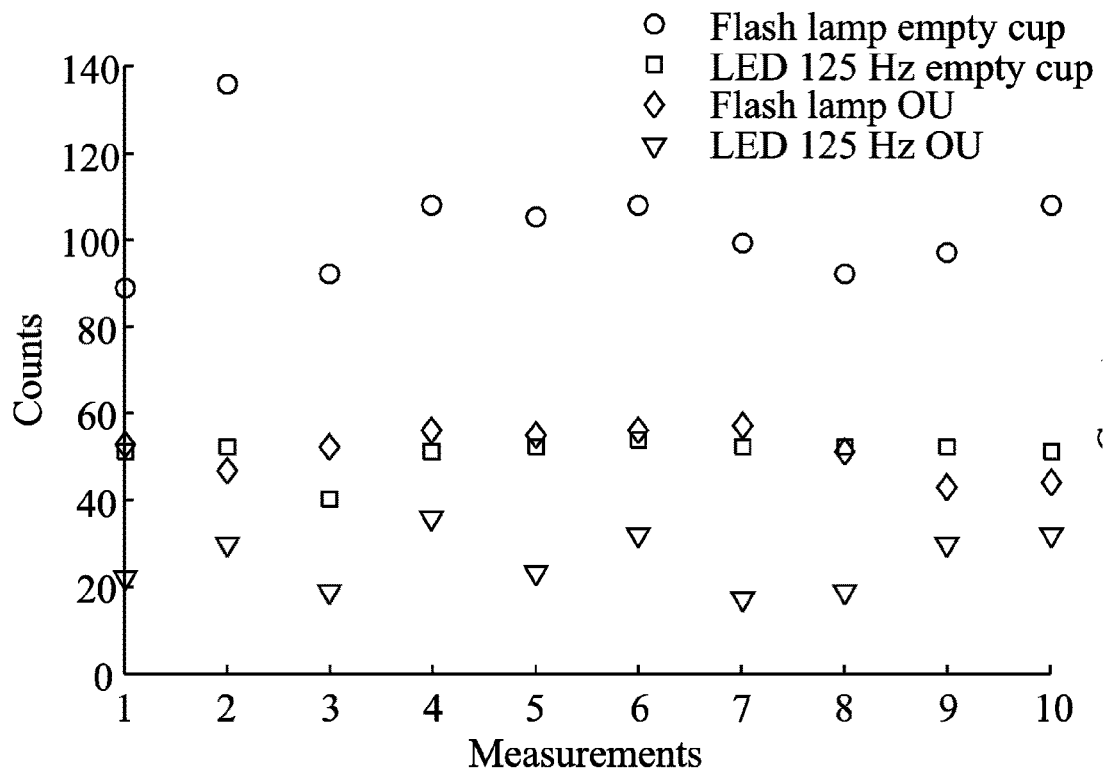
FIG. 12 a graph of repetitive measurements of different contributions to the background counts.
Figure 13:
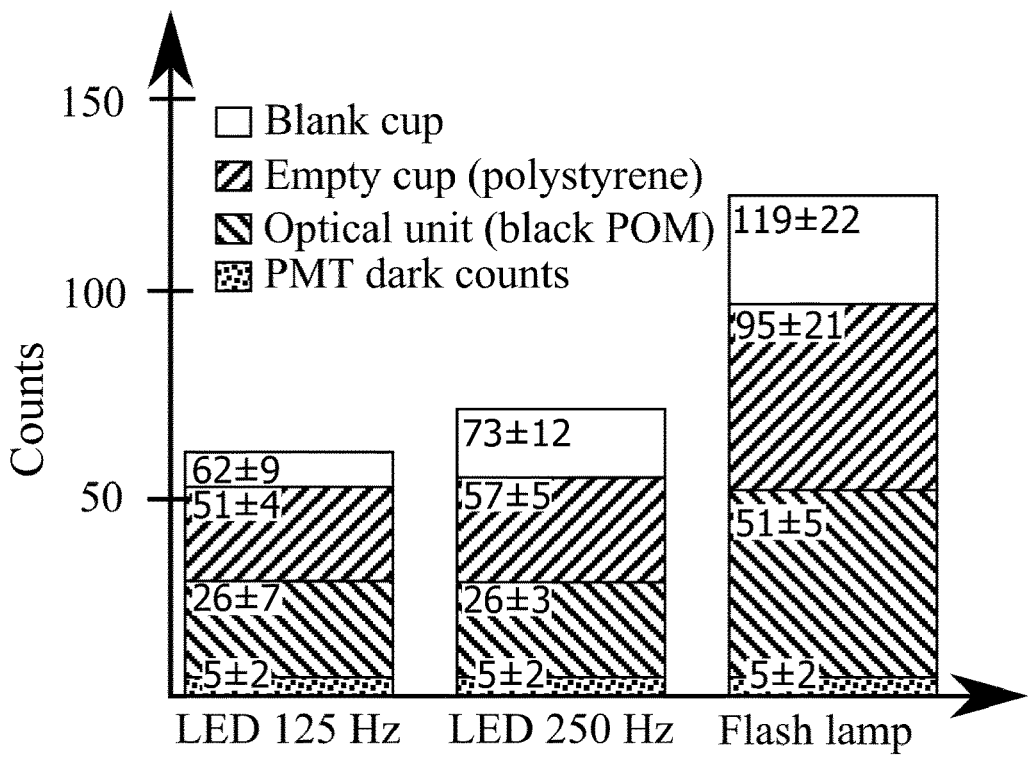
FIG. 13 a graph with a break-up of four different contributions to the background counts for three different excitation modes.

FIGS. 12 and 13 compare the background of the LED- and flash lamp based systems. FIG. 12 shows data from repetitive measurements of background from the optical unit itself, measured with a black POM closed volume fixture and background from empty cup measured with flash lamp excitation and LED excitation at 125 Hz. FIG. 13 shows the background for LED 125 Hz, 250 Hz, and flash lamp excitation; four contributions are distinguished: PMT dark counts, optical unit, empty cup (polystyrene only) and processed cup with null concentration. The background of optical unit itself was measured with a special light tight fixture made of black Polyoxymethylen (POM). The fixture is closed volume and has no cup inside. For the LED based optical unit operated at 125 Hz the background from the unit itself measured with black POM is 26±7 counts (including dark counts), measured with empty cup 51±4 counts, and 62±9 counts when measured on the blank cups (FIG. 12). The points in the figure are repetitive measurements performed on one fixture for the black POM and empty cup. In FIG. 13 the average values and standard deviations are calculated from the 10 repetitive measurements with closed volume black POM and empty cup; and with 15 replicates for blank cups. The flash lamp based optical unit exhibits 51±5 counts from the unit itself, 95±21 including the empty cup and 119±22 measured with the processed cup. The proportion of four contributions is approximately the same for two light sources but background in the LED unit is reduced by 52% and 39% for 125 Hz and 250 Hz operation, respectively. This background reduction is partially explained by LEDs absence of afterglow, comparing to the flash lamp. Xenon flash lamp exhibits afterglow for hundreds of microseconds, adding to background and decreasing SNR. The intensity of long-lived part of background which contributes to time gated measurements, also depends on the excitation pulse width. With longer pulse width, the number of molecules emitting unwanted light is lower and it drops faster if background lifetime is shorter than fluorophore lifetime. Furthermore, the LED emission spectrum is ten times narrower than the spectrum of the flash lamp based system. If the excitation spectrum of background is broadband, it has better spectral match with broadband flash lamp excitation.

Figure 14:
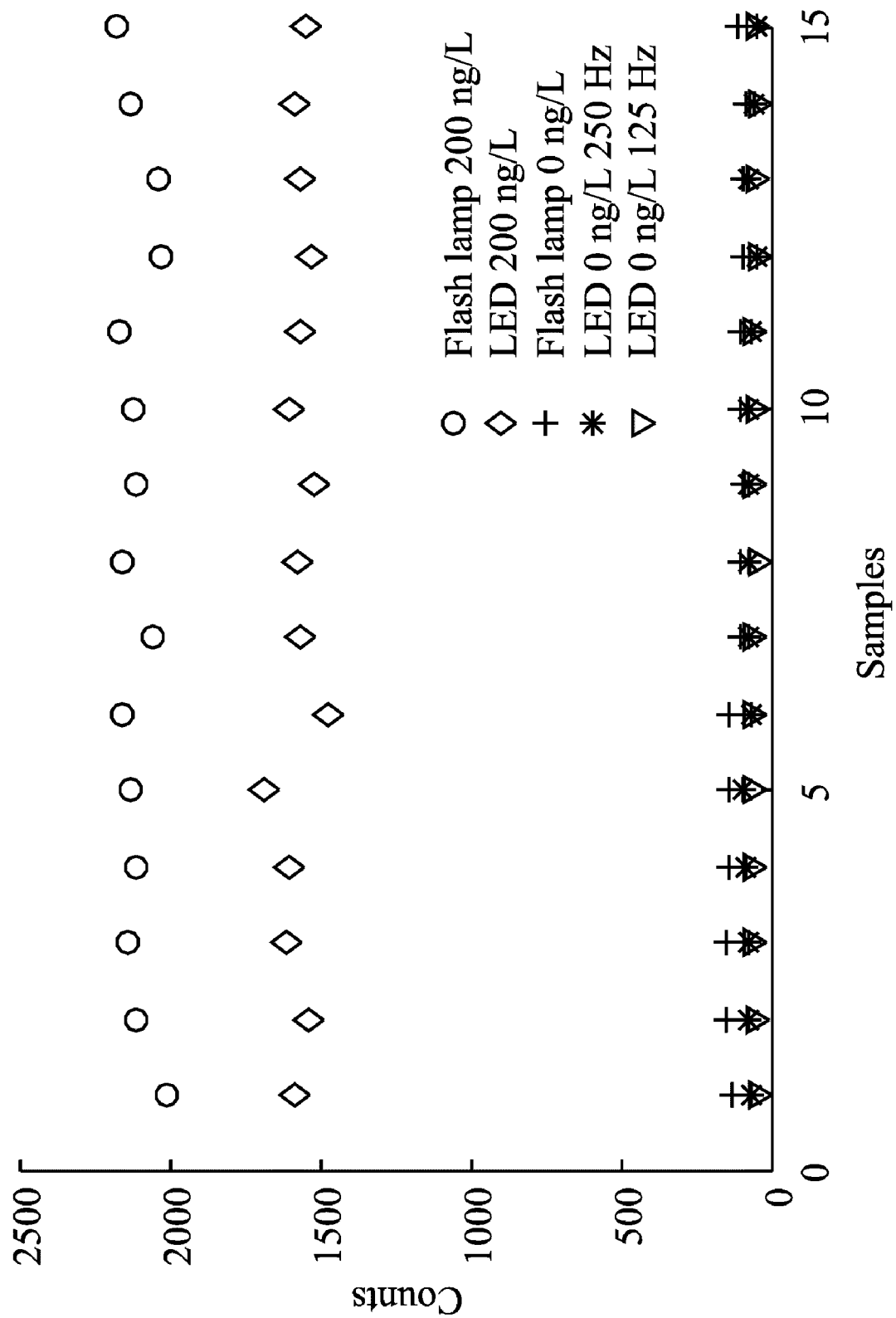
FIG. 14 a graph with fluorescence responses for 15 replicates comprising a sample derived from a solution with a known target concentration and 15 replicates of blank receptacles.

FIG. 14 shows the fluorescence response of 15 replicates with TnI 200 ng/L concentration and 15 blank cups processed with solution of null concentration, excited by the flash lamp system and by the LED system using equal excitation energy. Each point on the graph represents one measurement of one cup with 777 pulses.

Sample cups with the concentration of cardiac marker TnI of 200 ng/L were measured with both optical units with the same exposed energy. As noted above, FIG. 14 presents the data for 30 cups (15 sample and 15 blank cups) and Table 1 shows parameters of light sources and statistical data. The samples were exposed to 777 pulses with pulse energy 5.1 µJ each and with 250 Hz (125 Hz) repetition frequency, what corresponds to 1.27 mW (0.64 mW) average power. The LED based optical unit was tested with two repetition frequencies. The average counts are given with confidence intervals for sample mean that are calculated using t-parameter Student's distribution as $$\bar{x} \pm t \frac{s}{\sqrt{n}},$$

with $\bar{x}$ as sample mean, s as sample standard deviation, and n being sample size. The parameter t is calculated with P of 2.5% corresponding to 95% confidence level. The sample standard deviations s are given with confidence intervals, which are calculated using $\chi^2$ distribution:

$$\sqrt{\frac{(n-1)s^2}{\chi^2_{\alpha/2}}} \leq \sigma \leq \sqrt{\frac{(n-1)s^2}{\chi^2_{1-\alpha/2}}}, \quad (6)$$

where α is the confidence level. For α of 95% and 15 samples, standard deviation confidence intervals are [0.73·s; 1.58·s] and are given in the Table 1. It should be noted that the sample size of 15 cups is not sufficient to have high statistical precision but it was not a goal in this investigation. It would require about 200 replicates to achieve confidence interval for standard deviation [0.91·s; 1.08·s] at 95% confidence level. CVS and CVB are coefficients of variation for the cups with 200 ng/L concentration and blank cups, respectively. It is calculated as a relation of sample standard deviation to its mean. The signal-to-background ratio is improved by 18% because the background is reduced with the LED excitation as discussed above. The fluorescence response of sample cups is 26% lower when excited with the LED unit. Thus, the SNR is decreased because the signal is decreased. Three differences in light sources contribute to the changed signal level: increased excitation pulse width, different spatial and spectral distribution. As discussed above the increased pulse width corresponds to signal reduction by 10%. Spectral overlap is by 19% better with LED excitation when other parameters constant. Enlarged illumination area can cause further signal reduction if chelates distribution in the cup is non-uniform. Depending on the exact chelates distribution, three times larger illumination area can be disadvantageous if chelates are concentrated more in the center. It was observed that misalignment of the flash lamp image by several millimeters in the instrument so that is it not centered but placed on the edge of the cup, decreases signal by up to 30% comparing to aligned setup.

TABLE 1

Parameters of excitation light and efficiency presented for sample concentration of 200 ng/L and null concentration. The LED was used with two repetition frequencies of 250 and 125 Hz with constant pulse energy. Data calculated for 15 replicates.

|  | Signal (TnI 200 ng/L) | | | Background (0 ng/L) | | |
| --- | --- | --- | --- | --- | --- | --- |
|  | Flash lamp | LED | | Flash lamp | LED | |
| Average power, mW | 1.27 | 1.27 | 0.64 | 1.27 | 1.277 | 0.637 |
| Number of pulses | 777 | 777 | 777 | 777 | 777 | 777 |

TABLE 1-continued

Parameters of excitation light and efficiency presented for sample concentration of 200 ng/L and null concentration. The LED was used with two repetition frequencies of 250 and 125 Hz with constant pulse energy. Data calculated for 15 replicates.

| | Signal (TnI 200 ng/L) | | | Background (0 ng/L) | | |
|---|---|---|---|---|---|---|
| | Flash lamp | LED | | Flash lamp | LED | |
| Frequency, Hz | 250 | 250 | 125 | 250 | 250 | 125 |
| Pulse energy, μJ | 5.1 | 5.1 | 5.1 | 5.1 | 5.1 | 5.1 |
| Average counts (±95% CI) | 2114.1 ± 28.6 | 1574.3 ± 26.8 | 1508.9 ± 34.8 | 119.1 ± 12.4 | 73.3 ± 7.1 | 62.1 ± 5.2 |
| Sample standard deviation [±95% CI] | 51.6 [37.8; 81.4] | 48.3 [35.4; 76.2] | 62.8 [46.0; 99.0] | 22.4 [16.4; 35.3] | 12.9 [9.4; 20.3] | 9.3 [6.8; 14.7] |
| $CV_{S(B)}$ | 2.4% | 3.1% | 4.2% | 18.8% | 17.5% | 15.0% |
| S/B @200 ng/L | 17.7 | 21.5 | 24.3 | | | |
| SNR @200 ng/L | 35.5 | 30.0 | 22.8 | | | |

Figure 15:
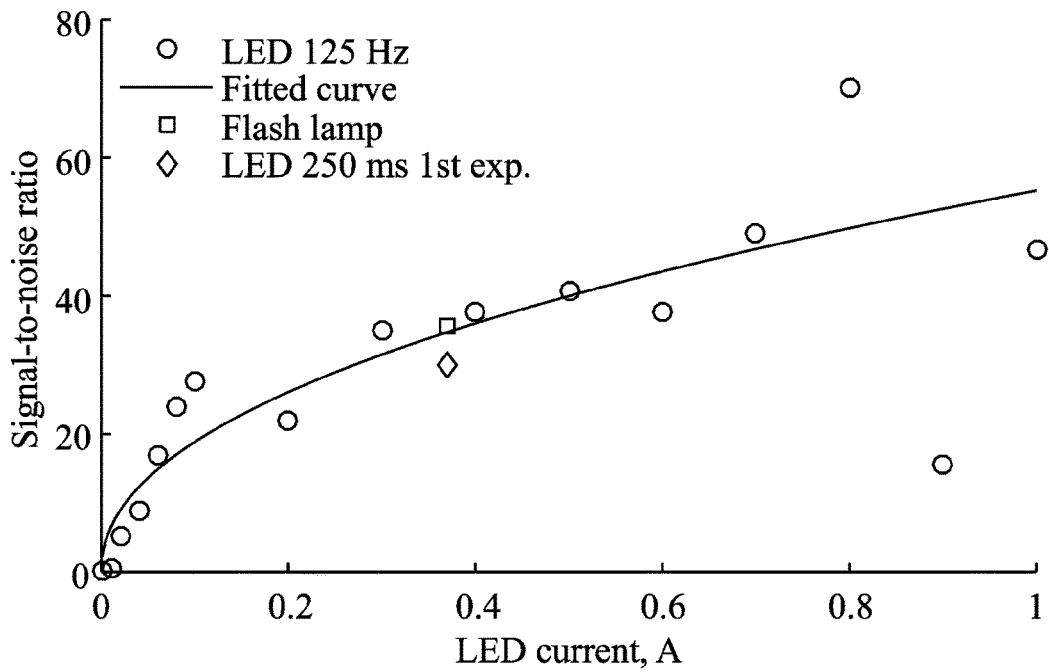
FIG. 15 a graph of the signal-to-noise-ratio as a function of excitation pulse energy (LED current); and in FIG. 16 a graph of background counts from blank and empty receptacles as a function of LED current.
Figure 16:
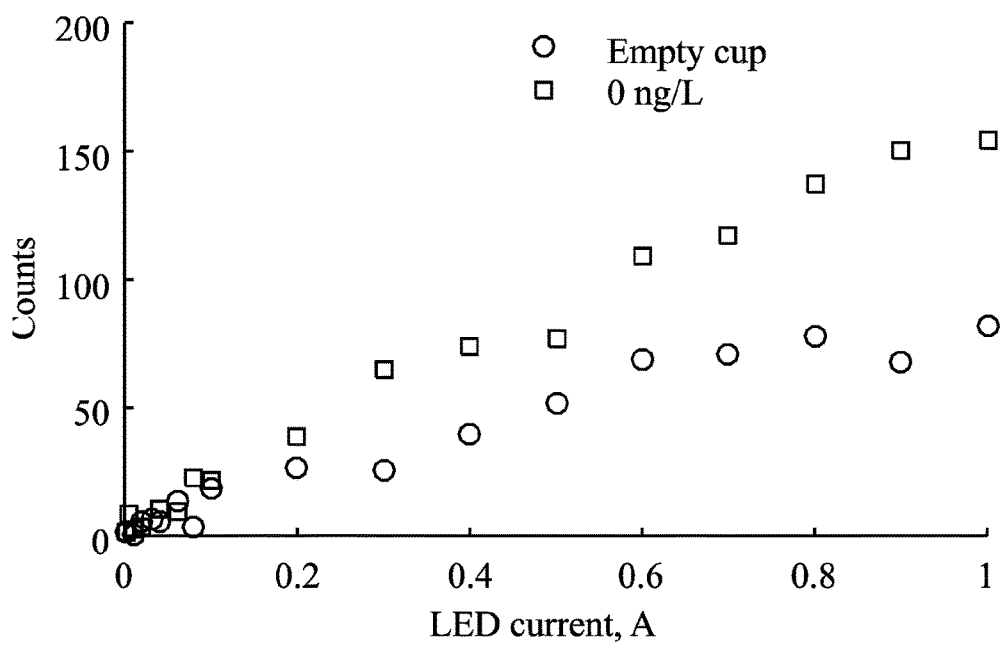

Keeping excitation energy constant, the SNR can be improved by decreasing illumination area in the cup thus having higher fluorescence signal. Decreasing the excitation pulse width will increase the signal however maximum reaching 10% improvement. Better spectral overlap with chelate excitation spectrum centered at 340 nm, will further improve the signal. The SNR can also be improved increasing excitation energy. FIG. 15 shows the signal-to-noise ratio averaged for four cups vs. LED current (excitation pulse energy) for a TnI concentration of 200 ng/L. The SNR grows with the square root with excitation power; squares and diamonds show mean values for the experiment with 15 replicates for the flash lamp and LED based unit, respectively. FIG. 15 illustrates SNR as a function of LED current at TnI concentration of 200 ng/L, where it grows with a square root dependence (fitted solid curve). The SNR was calculated for four replicates, shown as circles. The behaviour is explained by Poisson distributed signal and noise in the system, with standard deviation of the distribution equal to its mean. The values calculated with experiment with 15 replicates (Table 1) is shown as squares for flash lamp excitation and as diamonds for the LED unit at 250 Hz, respectively. Higher statistical precision can be achieved investigating a larger number of samples. If only background variation is considered in equation 4, the SNR grows rapidly when signal is comparable to detection system noise and then reaches a plateau when it is independent on excitation power. This happens because a significant part of background comes from non-specific binding when the tracer molecules are bound to the cup walls. In this case the chelates concentration is very low and the background variation is in the part of square root curve that can be approximated as linear. Signal-to-background ratio does not depend on excitation power as well, because background grows linearly with excitation power. FIG. 16 shows background counts from a blank cup and an empty cup as function of LED current (LED excitation).

The background of the blank and empty cups grows with excitation power as shown in FIG. 16. The SNR ratio can thus be improved by increasing excitation power, and by tuning the spectral, spatial and temporal characteristics of the sample illumination.

The invention claimed is:

1. A system adapted for time-resolved fluoroimmunoassay detection comprising:
    a receptacle with a sample volume adapted for receiving a sample therein;
    a light emitting diode (LED) light source adapted to emit pulsed excitation light;
    illumination optics adapted to collect the pulsed excitation light from the LED light source and to deliver said pulsed excitation light to the sample volume in the receptacle;
    a detection device adapted for gated detection of fluorescence radiation at least in a detection spectral range;
    detection optics adapted to collect fluorescence radiation from the receptacle at least in the detection spectral range and deliver said fluorescence radiation to the detection device; and
    an optical filter device configured for a separation of excitation light and detection light;
    wherein
    the LED light source has a peak intensity emission at a wave length below 345 nm;
    the system further comprises a control unit configured to at least control a timing of a detection cycle, the detection cycle comprising an excitation pulse emitted by the LED light source, followed by a detection period for the detection of fluorescence radiation by the detection device,
    wherein the detection period is separated from the excitation pulse by a detection delay;
    wherein a pulse duration of the excitation pulse is at least 10 μs;
    wherein the detection delay is between 200 μs and 600 μs; and
    wherein the illumination optics is an imaging optics arranged to project an image of the LED light source on an image plane in the sample volume formed on the bottom of the receptacle.

2. The system according to claim 1, wherein a pulse duration of the excitation pulse is at least 50 μs.

3. The system according to claim 1, wherein the pulse duration of the excitation pulse is up to 500 μs.

4. The system according to claim 1, wherein the detection period is between 100 μs and 500 μs.

5. The system according to claim 1, wherein the light emitting diode has a peak intensity emission at a wave length of at least 320 nm.

6. The system according to claim 1, wherein the receptacle is a well on a microplate.

7. The system according to claim 1, wherein the detection delay is between 300 μs and 500 μs.

8. The system according to claim 1, wherein the LED light source has a spectral emission with a full width at half maximum (FWHM) between 10 nm and 20 nm.

* * * * *